United States Patent [19]
Kato et al.

[11] Patent Number: 5,120,715
[45] Date of Patent: Jun. 9, 1992

[54] METHOD FOR PURIFYING FIBROBLAST GROWTH FACTOR PROTEIN

[75] Inventors: Koichi Kato, Kawanishi; Kenji Kawahara, Izumi; Tomoko Kajio, Minoo, all of Japan

[73] Assignee: Takeda Chemical Industries, Ltd., Osaka, Japan

[21] Appl. No.: 443,896

[22] Filed: Nov. 30, 1989

[30] Foreign Application Priority Data

Dec. 12, 1988 [JP] Japan ................. 63-314168

[51] Int. Cl.⁵ ............ C12N 15/00; C07K 3/20; C07K 13/00; C12P 21/02
[52] U.S. Cl. ............... 514/21; 514/2; 514/54; 514/57; 514/802; 530/399; 530/350; 530/413; 530/383
[58] Field of Search ............. 514/54, 57, 59, 2, 21, 514/802; 530/399, 350, 413, 383

[56] References Cited

U.S. PATENT DOCUMENTS

| | | |
|---|---|---|
| 4,083,961 | 4/1978 | Dussourd'Hinterland et al. .................. 514/59 |
| 4,785,079 | 11/1988 | Gospodarowicz et al. ........ 530/417 |
| 4,789,733 | 12/1988 | Winkelman ...................... 530/383 |
| 4,798,886 | 1/1989 | Kato et al. ...................... 435/69.3 |
| 4,840,941 | 6/1989 | Ueno et al. ...................... 514/59 |
| 4,999,340 | 3/1991 | Hoffman et al. .................. 514/57 |
| 5,002,934 | 3/1991 | Norton et al. .................... 514/54 |
| 5,006,642 | 4/1991 | Newman et al. .................. 530/413 |

FOREIGN PATENT DOCUMENTS

| | | |
|---|---|---|
| 237966 | 9/1987 | European Pat. Off. . |
| 281822 | 9/1988 | European Pat. Off. . |
| 0287470 | 10/1988 | European Pat. Off. . |

OTHER PUBLICATIONS

Huang, et al., The Journal of Biological Chemistry, 261(25):11600-11607 (1986).
Research Disclosure, Feb. 1989 "Application of Sulfated Polysaccharide Gel for Affinity Chromatography."
A pamphlet of Sulfated Cellulofine (Seikagaku Kogyo Co.).
J. Biol. Chem. 261, 1924-1928 (1986), R. Lobb, et al.
M. Senoo, et al., Biochemical and Biophysical Research Communications, 151, 701-708 (1988).

Primary Examiner—Ronald W. Griffin
Attorney, Agent, or Firm—David G. Conlin; David S. Resnick; Ernest V. Linek

[57] ABSTRACT

Disclosed is a method for purifying a fibroblast growth factor (FGF) protein with use of a crosslinked polysaccharide sulfate. The FGF protein is preferable a mutein, in which at least one human basic FGF-constituent amino acid is substituted by at least one different amino acid. The crosslinked polysaccharide sulfate is preferably a crosslinked cellulose sulfate, a crosslinked agarose sulfate or a crosslinked dextran sulfate. According to the present invention, FGF can be highly purified on a commercial scale, and therefore preparations containing the FGF protein can be advantageously formulated.

5 Claims, 1 Drawing Sheet

METHOD FOR PURIFYING FIBROBLAST GROWTH FACTOR PROTEIN

BACKGROUND OF THE INVENTION

The present invention relates to a method for purifying fibroblast growth factor (hereinafter also briefly referred to as FGF) proteins.

FGF was first isolated as a factor exhibiting strong growth promoting action on fibroblasts such as BALB/c3T3 cells [D. Gospodarowicz, Nature 249, 123 (1974)]. It is now known that the FGF exhibits growth promoting action on almost all cells derived from mesoblast. FGF is classified into basic FGF (hereinafter briefly referred to as bFGF) and acidic FGF (hereinafter briefly referred to as aFGF), based on the isoelectric point thereof. bFGF and aFGF both have strong growth promoting action and plasminogen activator inducing action on vascular endothelial cells. Together, these actions suggest a potential for the application thereof as a drug for promoting angiogenesis, as a therapeutic drug for traumas, and as a preventive and therapeutic drug for thrombosis, arteriosclerosis, etc.

Previously, the FGFs were purified to homogeneity from organs derived from animals, such as bovine pituitary. However, supply of these FGFs was limited, and there was a fear of antigenicity due to their heterozoic origin. The FGFs were also obtained from culture supernatants of various animal cell lines, but their supply was also limited. Recently, there has been developed a method for producing FGF in large quantities. The method involves using recombinant DNA techniques to express a cloned human FGF gene in microorganisms or in animal cells. [*FEBS Letters* 213, 189-194 (1987); European Patent Publication (hereinafter also referred to as EP Publication) No. 237,966)].

FGFs have been purified using heparin affinity column chromatography [*Science* 223, 1296-1299 (1984); *Journal of Biological Chemistry* 261, 1924-1928 (1986)]. FGFs have been purified using heparin affinity column chromatography, from bovine and human brain; bovine pituitary; bovine retina; bovine, human and avian cartilage; rat chondrosarcoma culture supernatant; human melanoma culture supernatant; and human hepatoma culture supernatant [*Journal of Biological Chemistry* 261, 1924-1928 (1986)].

The heparin affinity column chromatography has also been used for the purification of the FGF prepared by the recombinant DNA technique [*Biochemical and Biophysical Research Communications* 146, 470-477 (1987)].

However, the carrier used in the heparin affinity column chromatography discussed above, such as a conjugate of crosslinked agarose and heparin, has several disadvantages: (1) heparin is liable to be liberated from the carrier (crosslinked agarose), and (2) the carrier undergoes serious deterioration with repeated use. Heparin affinity column chromatography is therefore unsuitable for the purification of FGF on a large scale commercial production.

SUMMARY OF THE INVENTION

The primary object of the present invention to provide a method for purifying FGF protein suitable for use on a commercial scale.

Other objects of this invention will be apparent from the following description and the accompanying drawing.

The present inventors have discovered that a crosslinked polysaccharide sulfate is an excellent carrier for use in the purification of the FGF protein on a commercial scale.

In accordance with the present invention, there is provided a method for purifying fibroblast growth factor (FGF) protein, which comprises treating a material containing crude FGF protein with a crosslinked polysaccharide sulfate.

DESCRIPTION OF THE PREFERRED EMBODIMENTS

Figure 1:
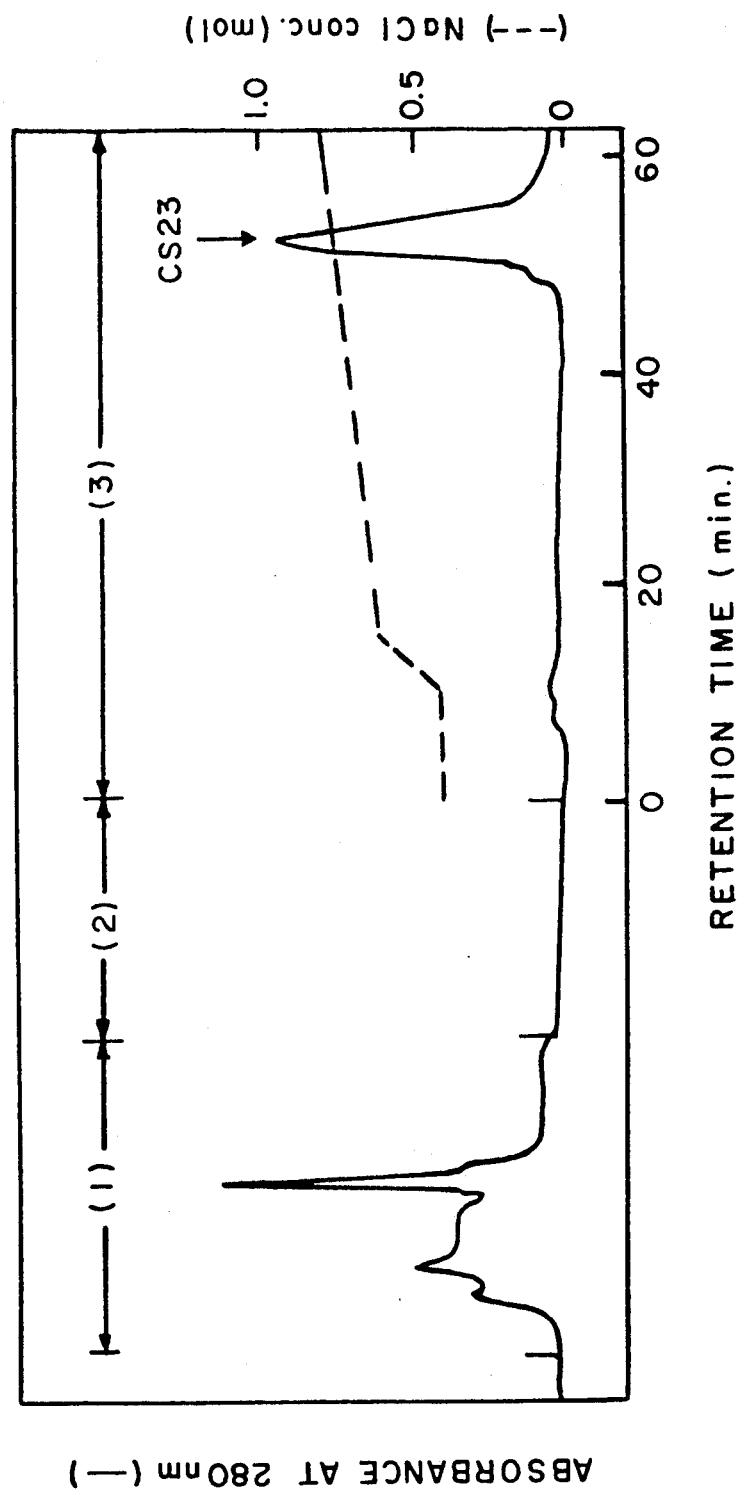
FIG. 1 is a graph showing an elution pattern obtained in Example 1.

The FGF proteins used in the present invention may include basic FGF (hereinafter also referred to as bFGF) and acidic FGF (hereinafter also referred to as aFGF). In particular, the bFGF is preferred.

The term "FGF protein" used in the specification and claims means a polypeptide or protein having FGF activity.

The FGF protein used in the present invention include those derived from mammals. The mammals include human, monkey, pig, bovine, sheep and horse.

The FGF proteins include those extracted from various organs in which the presence of FGFs is already known, such as brain and pituitary.

Further, the FGF proteins include those obtained by the recombinant DNA technique [PCT International Publication No. WO/87/01728; *FEBS Letters* 213, 189-194 (1987); European Patent Publication No. 237,966]. Hereinafter, the recombinant human basic FGF may be referred to as rhbFGF.

The FGF proteins used in the present invention may include a FGF mutein.

Examples of the muteins of the FGFs used in the present invention include the muteins disclosed in European Patent Publication No. 281,822, *Biochemical and Biophysical Research Communications* 151, 701-708 (1988) and European Patent Publication No. 326,907.

For example, the FGF muteins used in the present invention are obtained essentially by variations of the amino acid sequences of the original peptides or proteins. Such variations include addition of amino acid(s), deletion of constituent amino acid(s) and substitution of constituent amino acid(s) by different amino acid(s).

Such addition of amino acid(s) includes addition of at least one amino acid.

Such deletion of constituent amino acid(s) includes deletion of at least one FGF-constituent amino acid.

Such substitution of constituent amino acid(s) by different amino acid(s) includes substitution of at least one FGF-constituent amino acid by at least one different amino acid.

At least one amino acid in the mutein which has at least one amino acid added to the FGF excludes methionine derived from the initiation codon used for peptide expression and a signal peptide.

The number of the added amino acid(s) is at least one. However, it may be any number as long as FGF characteristics are not lost. More preferable amino acids include some or all of the amino acid sequences of proteins which have homology with the FGFs and which exhibit activities similar to those of the FGFs.

As for the number of the deleted FGF-constituent amino acid(s) in the mutein which lacks at least one FGF-constituent amino acid, it may be any number as long as FGF characteristics are not lost.

As for the number of FGF-constituent amino acids prior to substitution in the mutein, which has at least one FGF-constituent amino acid substituted by at least one different amino acid, it may be any number as long as FGF characteristics are not lost.

Examples of the constituent amino acids prior to substitution include cysteine and cystine, but cysteine is preferable. The constituent amino acids other than cysteine prior to substitution include aspartic acid, arginine, glycine and valine.

When the constituent amino acid prior to substitution is cysteine, neutral amino acids are preferable as the substituted amino acids. The neutral amino acids include glycine, valine, alanine, leucine, isoleucine, tyrosine, phenylalanine, histidine, tryptophan, serine, threonine and methionine. Serine and threonine are particularly preferred.

When the constituent amino acid prior to substitution is any one other than cysteine, amino acids which are different, for example, in hydrophilicity, hydrophobicity or electric charge from the amino acid prior to substitution are selected as the substituting different amino acids. Specifically, when the amino acid prior to substitution is aspartic acid, the substituting amino acids include asparagine, threonine, valine, phenylalanine and arginine. In particular, asparagine and arginine are preferable.

When the amino acid prior to substitution is arginine, the substituting amino acids includes glutamine, threonine, leucine, phenylalanine and aspartic acid. Glutamine is especially preferable.

When the amino acid prior to substitution is glycine, the substituting amino acids include threonine, leucine, phenylalanine, serine, glutamic acid and arginine. Threonine is particularly preferred.

When the amino acid prior to substitution is serine, the substituting amino acids include methionine, alanine, leucine, cysteine, glutamine, arginine and aspartic acid. In particular, methionine is preferable.

When the amino acid prior to substitution is valine, the substituting amino acids include serine, leucine, proline, glycine, lysine and aspartic acid. Serine is especially preferred.

As the original constituent amino acids prior to substitution, aspartic acid, arginine, glycine, serine and valine are preferably selected.

As the substituted amino acids, asparagine, glutamine, arginine, threonine, methionine, serine and leucine are preferably selected.

The most preferred substituted muteins include a mutein in which cysteine, the constituent amino acid, is substituted by serine.

In the above substitution, the substitution of at least two constituent amino acids may be simultaneously carried out. In particular, it is preferable to substitute two or three constituent amino acids.

The muteins may be obtained by a combination of two or three of the above-mentioned addition, deletion and substitution.

A mutein is preferable in which at least one human bFGF-constituent amino acid is substituted by at least one different amino acid. In particular, rhbFGF mutein CS23 is preferable in which cysteine residues at the 70- and 88-positions of human bFGF are substituted by serine residues, respectively. The amino acid positions of the above-mentioned human bFGF are numbered in turn by taking the N-terminal Met of the amino acid sequence shown in FIG. 1 of EP Publication No. 281,822 as the position one.

In order to produce the muteins, site-directed mutagenesis is employed. This technique is well-known and described in R. F. Lather and J. P. Lecoq, *Genetic Engineering*, pp. 31–50, Academic Press (1983). Mutagenesis directed to oligonucleotide is described in M. Smith and S. Gillam, *Genetic Engineering: Principles and Methods*, Vol. 3, pp 1–32, Plenum Press (1981).

The production of a structural gene which encodes the mutein is carried out, for example, by the steps of:

(a) hybridizing a single-stranded DNA comprising a single strand of the structural gene of FGF with a mutagenic oligonucleotide primer(the above-mentioned primer is complementary to a region, including a codon for cysteine, to be replaced by this single strand, or including an anti-sense triplet which forms a pair with this codon in some cases, provided this does not apply to disparity with other codon for the amino acid than the above codon, or with the anti-sense triplet in some cases.), (b) elongating the primer using DNA polymerase to form a mutational heteroduplex, and (c) replicating this mutational heteroduplex.

Then, phage DNA for transferring the mutagenized gene is isolated and introduced into a plasmid.

A suitable host is transformed with the plasmid thus obtained, and the obtained transformant is cultivated in a medium, thereby being capable of producing the mutein.

The crosslinked polysaccharide sulfates used in the present invention include crosslinked cellulose sulfates, crosslinked agarose sulfates and crosslinked dextran sulfates.

The above cellulose is a polysaccharide composed of glucose linked by $\beta$-1,4 bonds, and it is preferable to have a molecular weight of about 50,000 to 2,000,000. Specific examples thereof include crystalline cellulose Avicel (Asahi Chemical Industry, Japan) and Cellulofine (Chisso Corporation, Japan).

The above agarose is a polysaccharide which is the main component of agar, and has the recurring structure of D-galactosyl-($\beta 1 \rightarrow 4$)-3,6-anhydro-L-galactosyl-($\alpha 1 \rightarrow 3$). It is preferable that the agarose have a molecular weight of about 10,000 to 5,000,000. Specific examples thereof include Sepharose 2B, Sepharose 4B and Sepharose 6B (Pharmacia, Sweden).

The above dextran is a D-glucose polymer mainly comprising $\alpha$ (1$\rightarrow$6) bonds formed, for example, by the action of a microorganism such as *Leuconostoc mesenteroides* on sucrose. It is preferable to have an average molecular weight of about 1,000 to 40,000,000.

The crosslinked polysaccharide sulfates used in the present invention are prepared by treating crosslinked polysaccharides such as the above-mentioned dextran, agarose and cellulose, with known crosslinking agents such as epichlorohydrin and 2,3-dibromopropanol by the methods known in the art.

The crosslinked polysaccharides are commercially available and can be purchased from Pharmacia (Sweden) under the trade names of Sephadex G-10, Sephadex G-15, Sephadex G-25, Sephadex G-50 and Sephadex G-100 (crosslinked dextran), and under the trade names of Sepharose CL-2B, Sepharose CL-4B and Sepharose CL-6B (crosslinked agarose). Also, crosslinked cellulose can be purchased from Chisso, Japan, under the trade name of Cellulofine (crosslinked cellulose). The desired crosslinked polysaccharide sulfates can be synthesized by reacting known sulfating agents, such as chlorosulfonic acid and sulfuric anhydride esters, with these crosslinked polysaccharides.

A crosslinked cellulose sulfate can be purchased from Seikagaku Kogyo, Japan, under the trade name of Sulfated Cellulofine (crosslinked cellulose sulfate).

Examples of the crosslinked dextran sulfates include sulfated Sephadex.

Examples of the crosslinked agarose sulfates include sulfated Sepharose.

The crosslinked polysaccharide sulfates used in the present invention may be in the form of the corresponding salts. Examples of the salts include sodium, potassium, ammonium and trimethylammonium salts. In particular, the sodium salts are preferable.

The crosslinked polysaccharide sulfates used in the present invention are insoluble in water, and therefore it is preferred to use them in their gelatinous state by hydration.

The methods for purifying and obtaining the FGF protein using the crosslinked polysaccharide sulfates in the present invention include affinity chromatography described below.

FGF protein-containing solutions may include both FGF-containing solutions obtained by extraction from animal cells, and FGF protein-containing solutions obtained by recombinant DNA techniques. The protein containing solution may be previously partially purified by the methods known in the art, such as ion exchange chromatography, gel filtration, salting out and hydrophobic chromatography.

The FGF protein-containing solutions are aqueous media containing the FGF protein. The aqueous media include water and media, mainly composed of water, and are preferably adjusted to the pH range of about 3 to 10 with buffer solutions such as phosphate buffer, citrate buffer and Tris-hydrochloric acid buffer, to prevent inactivation of the FGFs.

The FGF protein-containing solution is next readjusted to a pH range of about 5.0 to 9.0, and then diluted with distilled water as required, so that the electric conductivity thereof is not more than about 15 m ℧, as required. The FGF protein-containing solution thus obtained is brought into contact with the crosslinked polysaccharide sulfate gel. For this purpose, both batch and column methods may be used. However, the column method is more suitable due to its simple operation. In the case of the column method, the crosslinked polysaccharide sulfate gel is previously charged into a column, and thereafter to equilibrate it the column, it is thoroughly washed with a suitable buffer solution such as 50 mM citrate buffer (pH 7.0) containing 0.4 M NaCl. The amount of the gel used depends on the nature of the loaded FGF protein-containing solution, but the range of about 1 to 50 ml gel per mg of FGF protein is preferable.

The above-mentioned FGF protein-containing solution is next loaded on the column. The loading speed is selected in the space velocity (S.V.) range of about 0.1 to 5.0. After loading, the column is thoroughly washed, and the ionic strength of the buffer solution is increased by a conventional method to elute the FGF protein. The fractions containing the FGF protein are pooled. In order to increase the ionic strength, a salt such as NaCl is added or a buffer solution high in concentration is used so that the electric conductivity is increased to at least about 15 m , preferably at least 30 m ℧. For elution, both batch elution and concentration gradient elution methods may be used. When the concentration gradient elution method is used, for example, the concentration of NaCl is gradually increased from about 0M to 2.0M, thereby conducting elution and recovery. Thus, highly-purified FGF protein can be obtained in a high yield.

According to the present invention, a purified FGF protein, free from pyrogens, and with a purity of at least 99% can be obtained in a recovery of 80 to 100%. The carriers used in the present invention have many advantages: they are inexpensive, they will not deteriorate, and they can resist long-term repeated use. The present invention, therefore provides a superior method for purifying the FGF protein on a commercial scale.

The FGF protein obtained by the present invention is free from pyrogens and has very high purity. Accordingly, the FGF protein can be formulated into preparations as is, or as pharmaceutical compositions such as injections, tablets, capsules, solutions and ointments with pharmacologically permissible carriers, excipients, diluents and the like, and can be safely administered parenterally or orally to warm-blooded animals such as human, bovine, horse, pig, dog, cat, rabbit, rat and mouse.

The forms of such preparations are preferably injections, frozen products and lyophilized products.

The FGF protein is formed into such preparations as the pharmaceutical compositions, in accordance with pharmaceutical preparing methods known in the art, and there are used pharmacologically permissible additives, diluents, excipients and the like, as required.

For example, aqueous solutions for injection are prepared by conventional methods using solvents such as aqueous solvents (for example, distilled water), water-soluble solvents (for example, physiological saline solution and Ringer solution) and oily solvents (for example, sesame oil and olive oil); or additives such as solubilizers (for example, sodium salicylate and sodium acetate), buffers (for example, sodium citrate and glycerin), isotonic agents (for example, glucose and invert sugar), stabilizers (for example, human serum albumin and polyethylene glycol), preservatives (for example, benzyl alcohol and phenol) and soothing agents (for example, benzalkonium chloride and procaine hydrochloride).

The solid preparations for injection can be prepared by conventional methods, for example, mixing therewith diluents (for example, distilled water, physiological saline solution and glucose), excipients (for example, carboxymethylcellulose (CMC) and sodium alginate), preservatives (for example, benzyl alcohol, benzalkonium chloride and phenol) and soothing agents (for example, glucose, calcium gluconate and procaine hydrochloride).

In the preparations for injection, there may be added monosaccharides such as glucose, amino acids, various salts and human serum albumin. In addition, there may be added isotonic agents, pH regulating agents, soothing agents and antiseptics, and thereby the stable effective preparations of the FGF protein can be formulated.

The purified FGF protein obtained by the methods described above has growth promoting action on fibroblasts, angiogenic activities, high stability and low toxicity. Accordingly, the FGF protein obtained by the present invention can be used as a healing promoter drug for burns, traumas, postoperative tissues and the like, or therapeutic drugs for thrombosis, arteriosclerosis, etc.

Also, they can be used as reagents for promoting cell cultivation.

When the purified FGF or the mutein thereof obtained by the methods of the present invention is used as the above-mentioned drugs, the FGF protein is administered, for example, to the above-mentioned warm-blooded animals in an appropriate amount ranging from about 1 ng/kg body weight to 100 μg/kg body weight daily, taking into account the route of administration, symptoms, etc.

Further, when the purified FGF protein obtained by the methods of the present invention is used as a reagent for accelerating the growth of cultured cells, the FGF protein is preferably added to a medium so as to be contained in an amount of about 0.01 to 10 μg per liter of medium, more preferably about 0.1 to 10 μg per liter of medium.

According to the purifying methods of the present invention, the FGF protein can be highly purified on a commercial scale, and therefore the preparations containing the FGF protein purified by the methods of the present invention can be advantageously formulated.

The transformant used in Reference Example 1, mentioned below, was deposited in the Institute for Fermentation, Osaka (IFO), Japan and in Fermentation Research Institute, Agency of Industrial Science and Technology, Ministry of International Trade and Industry (FRI), Japan. The accession number and the deposit date are shown in Table 1. As to the deposit in FRI, the accession number of FERM P-9409 was given to the deposit, and then this deposit was converted to the deposit under Budapest Treaty and the transformant has been stored at FRI under the accession number of FERM BP-1645. The transformant has been stored in FRI.

TABLE 1

| Transformant | IFO | FRI |
| --- | --- | --- |
| E. coli MM294/ pTB762 | IFO 14613 (May 27, 1987) | FERM P-9409 FERM BP-1645 (June 11, 1987) |

REFERENCE EXAMPLE 1

Preparation of Cell Extract and Preparation of Partially Purified rhbFGF Mutein CS23 Sample The transformant *Escherichia coli* MM294/pTB762 (IFO 14613, FERM BP-1645) obtained in Example 7(1) of EP Publication No. 281,822 was cultivated in M9 medium containing 1% glucose, 0.4% casamino acid and 8 μg/ml tetracycline. When the Klett value reached about 200, 3-β-indolyl-acrylic acid was added thereto so as to be contained in an amount of 25 μg/ml, and cultivation was further conducted for 4 hours. After cultivation, cells were collected, and 300 g the cells were suspended in 1.5 liter of 25 mM phosphate buffer (pH 6.0) containing 2 mM dithiothreitol (DTT), 0.1 mM phenylmethyl sulfonyl fluoride (PMSF) and 0.1 mM (p-amidinophenyl)methane sulfonyl fluoride (APMSF), followed by desrupting with glass beads (0.25 to 0.5 mm in diameter) at 5° C. Thus, a cell extract was obtained. This extract was centrifuged at 14,000 rpm (Beckman centrifuge, JA-14 rotor) for 30 minutes to give a supernatant. The pH of the supernatant was adjusted to pH 8 with 1N-NaOH and then passed through a DEAE-Toyopearl column (5 cm in diameter × 27 cm, 530 ml, Tosoh, Japan) equilibrated with 25 mM phosphate buffer (pH 7.6). The flow through and the washings, with 25 mM phosphate buffer (pH 7.6), were collected together. This fraction was adjusted to pH 6.1 with 1N-HCl, and the precipitate that formed was removed by centrifugation at 14,000 rpm (Beckman centrifuge, JA-14 rotor) for 30 minutes to give a supernatant. This supernatant was diluted 3 times with 25 mM phosphate buffer (pH 6.0), and then loaded onto a CM-Toyopearl column (10 cm in diameter × 12 cm, 950 ml, Tosoh, Japan) equilibrated with 25 mM phosphate buffer (pH 6.0). After washing the column with 25 mM phosphate buffer (pH 6.0), rhbFGF mutein CS23 was eluted using 25 mM phosphate buffer (pH 6.0) containing 1M NaCl to provide a partially purified rhbFGF mutein CS23 preparation.

EXAMPLE 1

The partially purified rhbFGF mutein CS23 preparation obtained in Reference Example 1 was diluted 3 times with distilled water, and then loaded onto a sulfated Cellulofine column (2 cm in diameter × 25 cm, 80 ml, Seikagaku Kogyo, Japan) equilibrated with 50 mM sodium citrate buffer (pH 7.0) containing 0.4 M NaCl. The column was washed with 50 mM sodium citrate buffer (pH 7.0) containing 0.4 M NaCl, and then the following NaCl concentration linear gradient elution was carried out:

Buffer A: 50 mM sodium citrate buffer(pH 7.0)
Buffer B: 2.0 M NaCl/50 mM sodium citrate buffer(pH 7.0)
Elution program: 0 minute, 20% B; 10 minutes, 20% B; 15 minutes, 30% B; 90 minutes, 45% B; 96 minutes, 80% B
Flow rate: 4.0 ml/minute
Detection wave length: 280 nm The elution pattern is shown in FIG. 1. Referring to FIG. 1, (1) indicates a loading step of the sample onto the column, (2) indicates a washing step of the column and (3) indicates an eluting step of rhbFGF mutein CS23 from the column.

It was found that a peak fraction eluted at a retention time between 50 and 60 minutes contained rhbFGF mutein CS23, so that this fraction was separately taken. The rhbFGF mutein CS23 obtained here was found to show a single band on SDS polyacrylamide gel electrophoresis, to be free from pyrogens and to be highly pure. The yield was calculated to be 95%.

The following references, which are referred to for their disclosures at various points in this application, are incorporated herein by reference.
Nature 249, 123 (1974)
FEBS Letters 213, 189–194 (1987)
European Patent Publication No. 237,966
Science 223, 1296–1299 (1984)
Journal of Biological Chemistry 261, 1924–1928 (1986)
Biochemical and Biophysical Research Communications 146, 470–477 (1987)
PCT International Publication No. WO/87/01728
European Patent Publication No. 281,822
Biochemical and Biophysical Research Communications 151, 701–708 (1988)
European Patent Publication No. 326,907
What is claimed is:

1. A method for purifying a fibroblast growth factor (FGF) protein, which comprises treating a material containing crude FGF protein with a crosslinked polysaccharide sulfate selected from the group consisting of a crosslinked cellulose sulfate and a crosslinked agarose sulfate.

2. A method as claimed in claim 1, wherein the FGF protein is a mutein in which at least one human basic FGF-constituent amino acid is substituted by at least one different amino acid.

3. A method as claimed in claim 2, wherein the FGF protein is a mutein in which cysteine residues at the 70- and 88-positions of human bFGF are substituted by serine residues.

4. A method as claimed in claim 1, wherein the crosslinked polysaccharide sulfate is a crosslinked cellulose sulfate.

5. A method as claimed in claim 1, wherein the purity of the purified protein is at least 99%.

* * * * *